(12) United States Patent
Miyake

(10) Patent No.: US 7,214,183 B2
(45) Date of Patent: May 8, 2007

(54) ENDOSCOPE APPARATUS HAVING AN INSERTION CHANNEL

(75) Inventor: Kiyoshi Miyake, Asaka (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/658,381

(22) Filed: Sep. 10, 2003

(65) Prior Publication Data
US 2004/0054254 A1 Mar. 18, 2004

(30) Foreign Application Priority Data
Sep. 13, 2002 (JP) ............................. 2002-268729

(51) Int. Cl.
*A61B 1/00* (2006.01)
(52) U.S. Cl. ...................... 600/131; 600/130; 600/104; 600/146
(58) Field of Classification Search ............... 604/104, 604/108, 112; 600/104–106, 114, 130, 131, 600/153, 154, 146
See application file for complete search history.

(56) References Cited

U.S. PATENT DOCUMENTS

| | | | | | |
|---|---|---|---|---|---|
| 3,897,775 | A | * | 8/1975 | Furihata | 600/131 |
| 4,598,698 | A | * | 7/1986 | Siegmund | 600/131 |
| 4,604,992 | A | * | 8/1986 | Sato | 600/108 |
| 4,649,904 | A | * | 3/1987 | Krauter et al. | 600/154 |
| 4,700,694 | A | * | 10/1987 | Shishido | 600/104 |
| 4,750,475 | A | * | 6/1988 | Yoshihashi | 600/153 |
| 4,765,312 | A | | 8/1988 | Sasa et al. | |
| 4,874,364 | A | * | 10/1989 | Morris et al. | 604/35 |
| 4,905,082 | A | * | 2/1990 | Nishigaki et al. | 348/73 |
| 4,934,340 | A | * | 6/1990 | Ebling et al. | 600/151 |
| 4,984,563 | A | * | 1/1991 | Renaud | 600/108 |
| 5,183,031 | A | * | 2/1993 | Rossoff | 600/131 |
| 5,314,070 | A | * | 5/1994 | Ciarlei | 206/570 |
| 5,373,317 | A | | 12/1994 | Salvati et al. | |
| 5,489,256 | A | * | 2/1996 | Adair | 600/133 |
| 5,531,664 | A | * | 7/1996 | Adachi et al. | 600/149 |
| 5,658,238 | A | * | 8/1997 | Suzuki et al. | 600/150 |
| 5,701,155 | A | * | 12/1997 | Wood et al. | 348/72 |
| 5,785,644 | A | * | 7/1998 | Grabover et al. | 600/131 |
| 5,873,814 | A | * | 2/1999 | Adair | 600/109 |
| 5,928,137 | A | * | 7/1999 | Green | 600/160 |
| 5,971,917 | A | * | 10/1999 | Komi et al. | 600/159 |
| 6,210,378 | B1 | * | 4/2001 | Ouchi | 604/264 |
| 6,221,007 | B1 | * | 4/2001 | Green | 600/160 |
| 6,315,712 | B1 | * | 11/2001 | Rovegno | 600/109 |
| 6,554,765 | B1 | * | 4/2003 | Yarush et al. | 600/132 |
| 6,569,084 | B1 | * | 5/2003 | Mizuno et al. | 600/102 |
| 2002/0022769 | A1 | * | 2/2002 | Smith et al. | 600/188 |
| 2003/0045778 | A1 | * | 3/2003 | Ohline et al. | 600/114 |
| 2003/0176880 | A1 | * | 9/2003 | Long et al. | 606/167 |

* cited by examiner

*Primary Examiner*—John P. Leubecker
(74) *Attorney, Agent, or Firm*—Dickstein Shapiro LLP

(57) ABSTRACT

A structure having a proximal open end for inserting a treatment instrument into a channel of the insertion portion that opens to a display panel side, and is provided on the frame of the display portion, wherein the treatment instrument inserted from the proximal open end (forceps-port) that extends out from the open end of the distal portion.

11 Claims, 21 Drawing Sheets

ENDOSCOPE APPARATUS HAVING AN INSERTION CHANNEL

CROSS-REFERENCE TO RELATED APPLICATIONS

This application is based upon and claims the benefit of priority from the prior Japanese Patent Application No. 2002-268729, filed Sep. 13, 2002, the entire contents of which are incorporated herein by reference.

BACKGROUND OF THE INVENTION

1. Field of the Invention

The present invention relates to an endoscope apparatus mainly used in the industrial field, which is inserted into a space, such as the inner space of a pipe, to inspect it.

2. Description of the Related Art

In general, an industrial endoscope has a slender insertion section, which is inserted into a to-be-inspected space, such as the inside of a pipe. In most cases, the proximal end of the insertion section is coupled to a hand-side operation section. A head portion is provided at the distal end of the insertion section. The head portion incorporates an observation optical system for observation, illumination optical system, etc. A bendable portion is provided behind the head portion. The directable section can be bent in vertical and horizontal directions. The tips of a plurality, e.g. 4, of bending wires are secured to the bendable portion. The proximal end of each bending wire is extended rearward (toward the hand-side). The end of the extended portion of each wire is coupled to a bending mechanism provided at the hand-side operation section.

Further, an operation knob is provided at the hand-side operation section. The operation knob is used to drive the bending mechanism and bend the bendable portion. When the operation knob is rotated, the bending mechanism is driven. When the bending mechanism is driven, the bending wires are pulled, thereby bending the bendable portion in the direction corresponding to the operation direction of the operation knob.

Also, an inner channel (treatment instrument insertion channel), through which a treatment instrument, such as forceps, is inserted, is formed in the endoscope. The front-side opening of the inner channel is situated in the head portion of the insertion section. Furthermore, the forceps port (proximal end opening) of the inner channel is situated in the operation section.

In accordance with recent bending mechanisms, which are motorized, bending may be performed using the manual operation knob, or switched to motorized bending means. For example, U.S. Pat. No. 5,373,317 discloses a bending-operation input means equipped with a joystick for generating a signal corresponding to an inclination angle.

BRIEF SUMMARY OF THE INVENTION

According to an aspect of the invention, there is provided an endoscope apparatus comprising:

a flexible slender insertion section inserted into a to-be-inspected space, the insertion section having a slender flexible tube portion, a distal portion coupled to a distal end of the flexible tube portion, a bendable portion coupled to the distal portion and to be bent, and a proximal portion coupled to a proximal end of the flexible tube portion; and an operation section coupled to a proximal end of the insertion section, the operation section having a grip portion gripped by an operator, and a bending operation portion which bends the bendable portion, wherein:

the insertion section has a treatment instrument channel, the distal portion of the insertion section having a distal open end of the treatment instrument channel, and the proximal portion of the insertion section having a proximal open end of the treatment instrument channel; and the proximal open end of the treatment instrument channel is located on the grip portion.

In the above structure, the bendable portion is bent by the bending operation portion of the operation section, while a treatment instrument, for example, is operated at the proximal open end of the treatment instrument channel of the grip portion near the being operation portion.

Preferably, the grip portion has a display portion which displays an observation image.

Thus, an observation image obtained by the endoscope apparatus can be displayed on the display portion of the grip portion.

More preferably, the display portion includes a display panel and a frame supporting the display panel, and the proximal open end of the treatment instrument channel is provided on the frame.

In this structure, the treatment instrument, for example, can be operated at the proximal open end of the treatment instrument channel located on the frame of the display panel of the display portion.

Also preferably, the proximal open end of the treatment instrument channel is located on the rear surface of the grip portion.

Accordingly, the treatment instrument, for example, can be operated at the proximal open end of the treatment instrument channel located on the rear surface of the grip portion.

Preferably, the grip portion has a grip which can be gripped by one hand of the operator.

Accordingly, the operator can grip the grip of the grip portion by one hand.

The grip portion may have an upper portion provided with a display portion which displays an observation image, the proximal open end of the treatment instrument channel being located below the display portion.

By virtue of this structure, the operator can operate the treatment instrument at the proximal open end of the treatment instrument channel located below the display portion, while observing an observation image displayed on the display portion located above the grip portion.

The grip portion may have a casing and a forceps-port constructing member, the forceps-port constructing member being coupled to the proximal open end.

This structure enables, for example, the treatment instrument to be inserted into the forceps-port constructing member located on the grip portion.

Further preferably, the forceps-port constructing member is located at a position at which the forceps-port constructing member does not interfere with an operation of the bending operation portion.

Therefore, for example, the treatment instrument can be inserted through the forceps-port constructing member without interfering with the operation of the bending operation portion.

The forceps-port constructing member may be located near the display portion and the bending operation portion.

This structure enables the treatment instrument to be inserted through the forceps-port constructing member, or the bending operation portion to be operated, while observing an observation image displayed on the display portion.

The frame of the display portion may have a side provided with a forceps port.

This structure enables, for example, the treatment instrument to be inserted through the forceps port at a side of the frame of the display portion.

The grip portion may have a downwardly opening forceps port formed in the lower end of the casing.

In this structure, even if the proximal end of the treatment instrument hangs down from the forceps port formed in the lower end of the casing of the grip portion, it does not interfere with the operation of the bending operation portion, since it hangs along the rear surface of the grip portion.

The grip portion may be detachable from the display portion.

This structure enables the weight of the grip portion to be reduced by detaching the display portion therefrom, which facilitates the operation of the grip portion.

The endoscope apparatus may further comprise a universal cord section and a case which can house the insertion section, the universal cord section and the operation section in a wound state.

In this structure, the insertion section, the universal cord section and the operation section can be housed in a wound state into the case, which means that the scope section can be housed easily after use.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
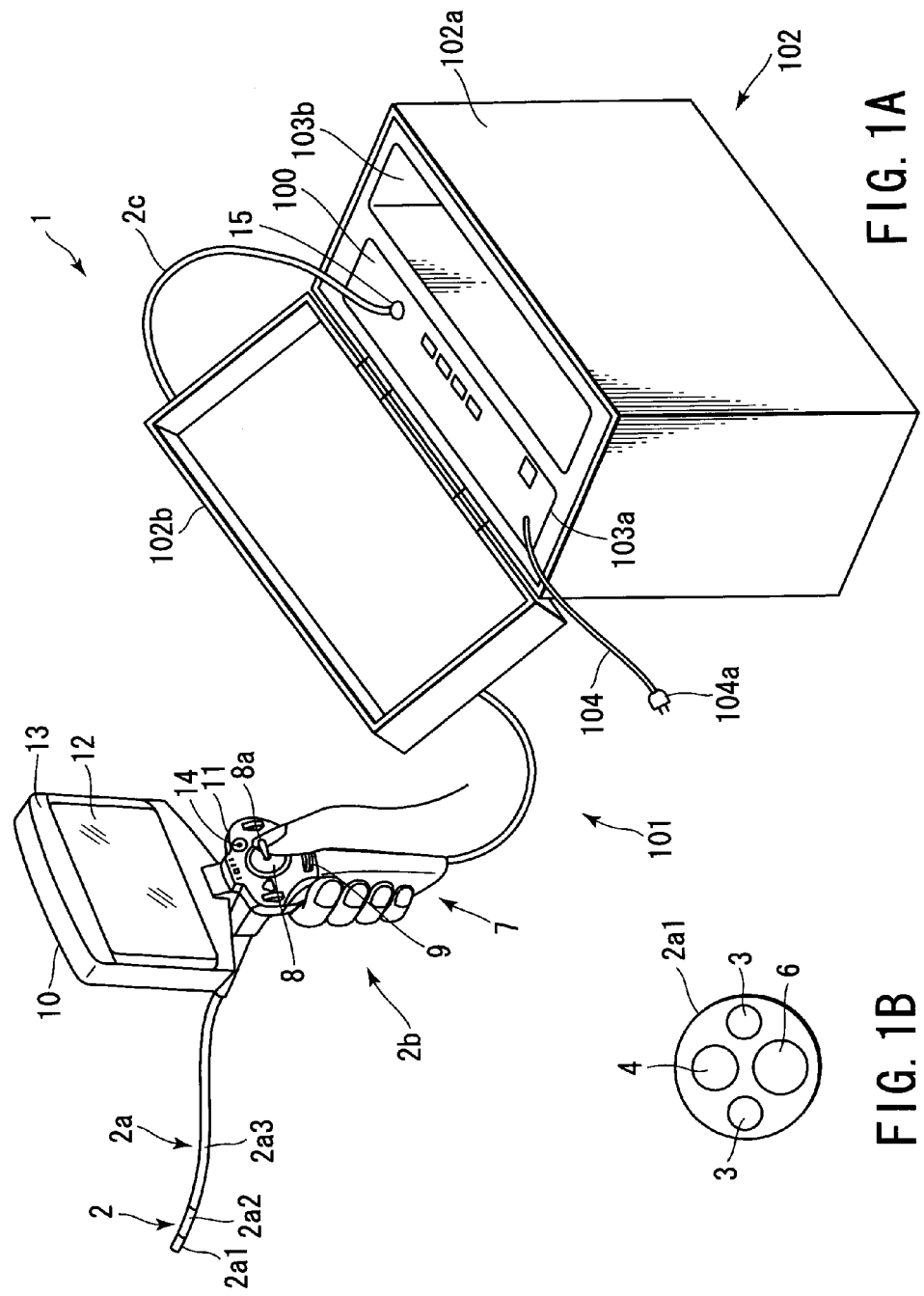
FIG. 1A is a schematic perspective view illustrating the entire structure of an industrial endoscope apparatus according to a first embodiment of the invention.
FIG. 1B is a plan view illustrating the top face of a head portion incorporated in the endoscope apparatus of the first embodiment.

Referring first to FIGS. 1A to 9, a first embodiment of the invention will be described. FIG. 1A shows an industrial endoscope apparatus 1 according to the first embodiment. The endoscope apparatus 1 comprises an endoscope main unit 101 and endoscope case 102. The main unit 101 is provided with all the structural elements of an endoscope. The main unit 101 is dismountably mounted in the case 102, and comprises a scope section 2 and stationary unit 100. The stationary unit 100 incorporates a light source apparatus, camera control unit (CCU), etc. The stationary unit 100 is connected to the proximal end of a power supply cord 104. The tip of the power supply cord 104 is connected to a plug 104a.

The scope section 2 at least comprises a flexible slender insertion section 2a to be inserted into a to-be-inspected space, operation section 2b and universal cord 2c. The insertion section 2a comprises a head portion 2a1 incorporating an observation optical system, illumination optical system, etc., a bendable portion 2a2 that can be bent by remote control, and a slender flexible tube portion 2a3. The bendable portion 2a2 is interposed between the head portion 2a1 and flexible tube portion 2a3.

Figure 3:
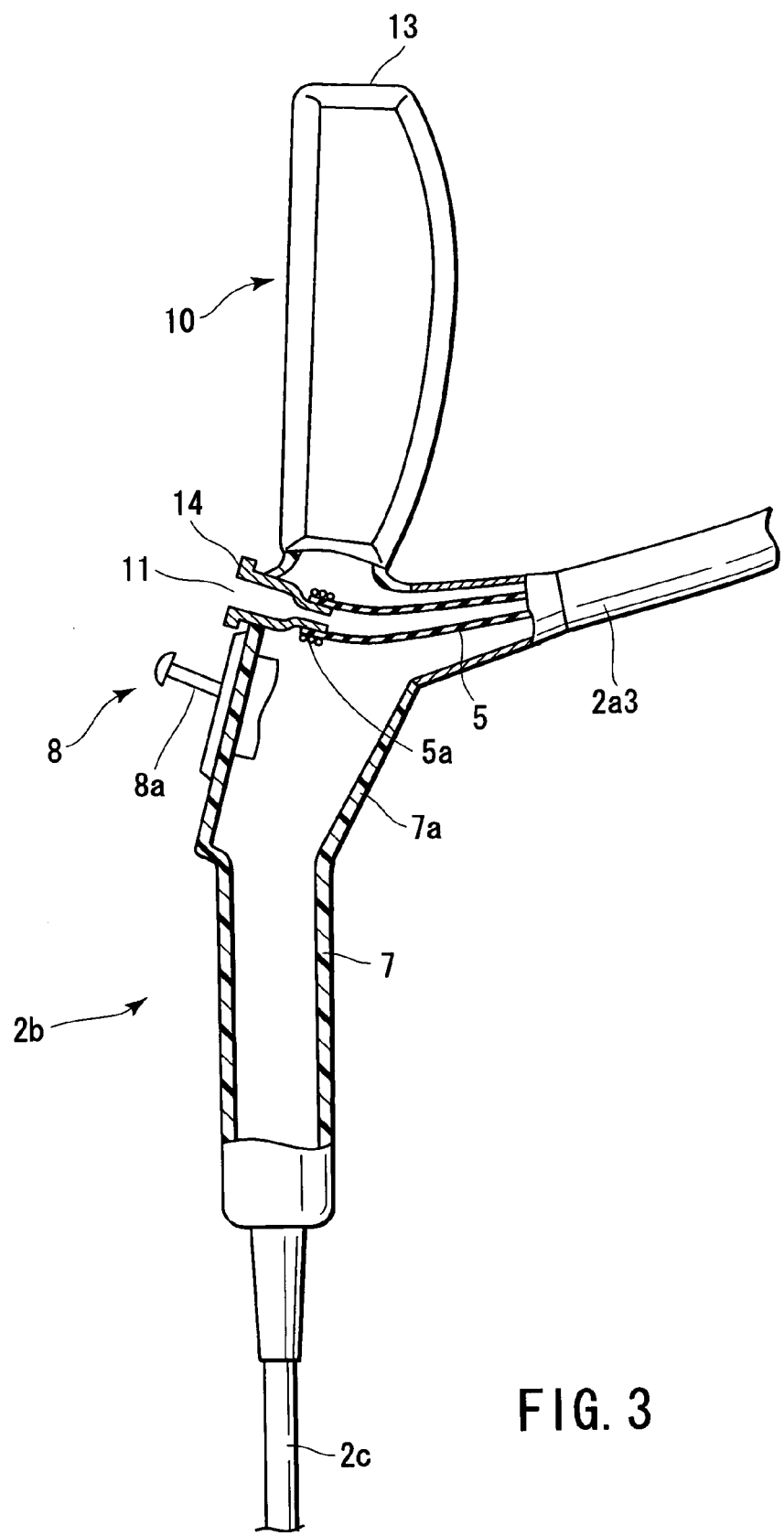
FIG. 3 is a side view partly in section illustrating the operation section of the endoscope apparatus of the first embodiment.

As seen from FIG. 1B, the front end of the head portion 2a1 is provided with an illumination window 3 for the illumination optical system, observation window 4 for the observation optical system, and the front open end 6 of an inner channel (treatment instrument insertion channel) 5 (see FIG. 3). The insertion section 2a contains a light guide for guiding illumination light to the illumination optical system, an electric cord connected to an image pickup element, such as a CCD, provided in the observation optical system, bending wires for bending the bendable portion 2a2, etc., which are not shown.

Figure 2:
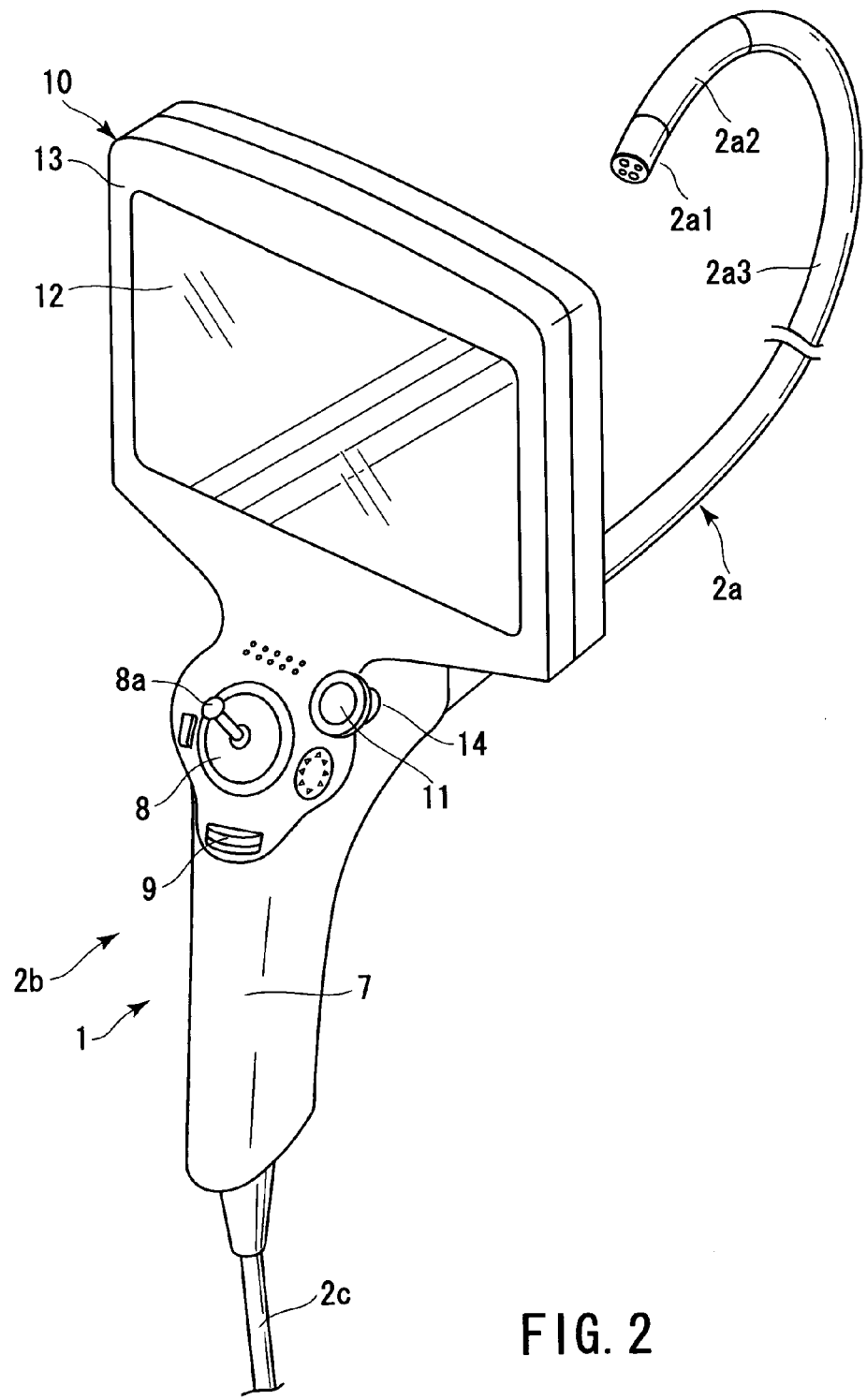
FIG. 2 is a perspective view illustrating the outward appearance of an operation section incorporated in the endoscope apparatus of the first embodiment.
Figure 4:
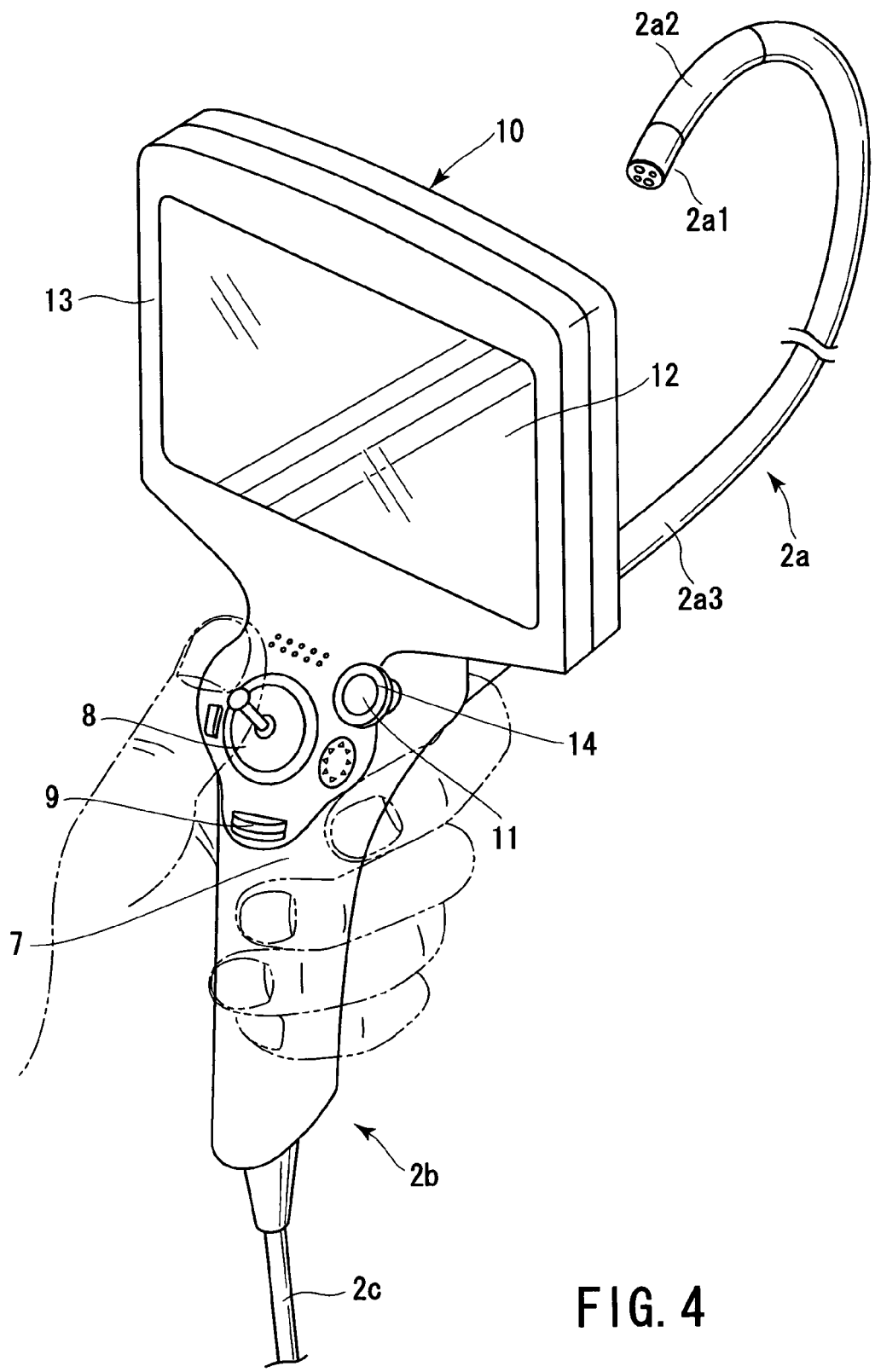
FIG. 4 is a perspective view illustrating a first state example in which the grip of the operation section incorporated in the endoscope apparatus of the first embodiment is gripped by one hand of an operator.

The proximal end of the flexible tube portion 2a3 is coupled to the front end of the operation section 2b. FIG. 2 shows the outward appearance of the operation section 2b. The operation section 2b comprises a grip portion 7 that can be gripped at least by one hand as shown in FIG. 4. The grip portion 7 mainly comprises a bending operation unit 8 and power button 9. The bending operation unit 8 has a joystick 8a. The bending operation unit 8 is motorized bending operation input means for bending the bendable portion 2a2 vertically and horizontally by pivoting the joystick 8a as a remote controller.

The proximal end of the joystick 8a of the bending operation unit 8 is pivotably supported on the point of support. The unit 8 generates a signal corresponding to the inclination angle of the joystick 8a.

A monitor section (display section) 10 and the forceps port (proximal opening end) 11 of the inner channel 5 are provided on the upper surface of the grip portion 7 of the operation section 2b. The monitor section 10 comprises a display panel 12, such as a liquid crystal display (LCD), and a frame 13 supporting the display panel 12.

As shown in FIG. 3, the monitor section 10 is located substantially parallel to the casing 7a of the grip portion 7. Alternatively, the monitor section 10 may be attached, inclined with respect to the grip portion 7. Further, a support mechanism capable of changing the inclination angle of the monitor section 10 may be attached to the casing 7a.

Further, a tubular forceps-port constructing member 14 is secured to the casing 7a of the grip portion 7. The forceps-port constructing member 14 is located between the monitor section 10 and bending operation unit 8, and provides the forceps port 11 of the inner channel 5. The proximal open end 5a of the inner channel 5 is coupled to the inner end of the forceps-port constructing member 14. The forceps-port constructing member 14 is located so as not to interfere the operation area of the bending operation unit 8. The forceps-port constructing member 14 may be located so that it opens toward the distal end of the grip portion 7 (i.e., toward the operator).

A coupling portion coupled to the front end of the universal cord 2c is provided at the distal end of the grip portion 7. A light guide, a plurality of electric cords, etc., which are not shown, are provided in the universal cord 2c. The light guide is extended from the insertion section 2a side. One of the electric cords is used to transmit an image signal output from the CCD. Another electric cord is connected to the display panel 12 of the monitor section 10.

A connector 15 is provided at the proximal end of the universal cord 2c. The connector 15 contains the connection end of the light guide, the connection terminals of the electric cords, etc. The connector 15 is disconnectably connected to the stationary unit 100.

The stationary unit 100 houses a power supply unit, light source unit, camera control unit, etc. When the connector 15 is connected to the stationary unit 100, the connection end of the light guide is connected to the light source unit. In this state, illumination light output from the light source unit enters the connection end of the light guide. Further, the connection terminals of the electric cords and the like of the connector 15 are connected to the camera control unit.

Image data indicative of an endoscopic observation image picked up by the CCD is converted into an electrical signal. This electrical signal is transmitted to the camera control unit via the electric cord. The camera control unit converts the electrical signal into a video signal. The signal output from the camera control unit is input to the display panel 12 of the monitor section 10. As a result, the endoscopic observation image is displayed on the display panel 12 of the monitor section 10.

The driving motor for bending the bendable portion 2a2 of the scope section 2 may be provided in the grip portion 7 of the operation section 2b, or in the connector 15, or in the stationary unit 100. If the driving motor of the bending mechanism is provided in the connector 15 or stationary unit 100, the member for transmitting the driving force of the driving motor, which is formed of, for example, an angle wire, is inserted in the universal cord 2c.

The endoscope case 102 comprises a box-shaped case main unit 102a and lid 102b. The case main unit 102a has an upper opening. The lid 102b is used to open and close the upper opening. The lid 102b is pivotably coupled to an edge of the upper opening of the main unit 102a by a hinge (not shown).

The interior of the main unit 102a is partitioned into two chambers 103a and 103b. The first chamber 103a contains the stationary unit 100 of the endoscope main unit 102. The insertion section 2a and operation section 2b of the scope section 2, and the universal cord 2c are housed in the second chamber 103b, for example, roughly bundled, when they are not used.

Figure 5:
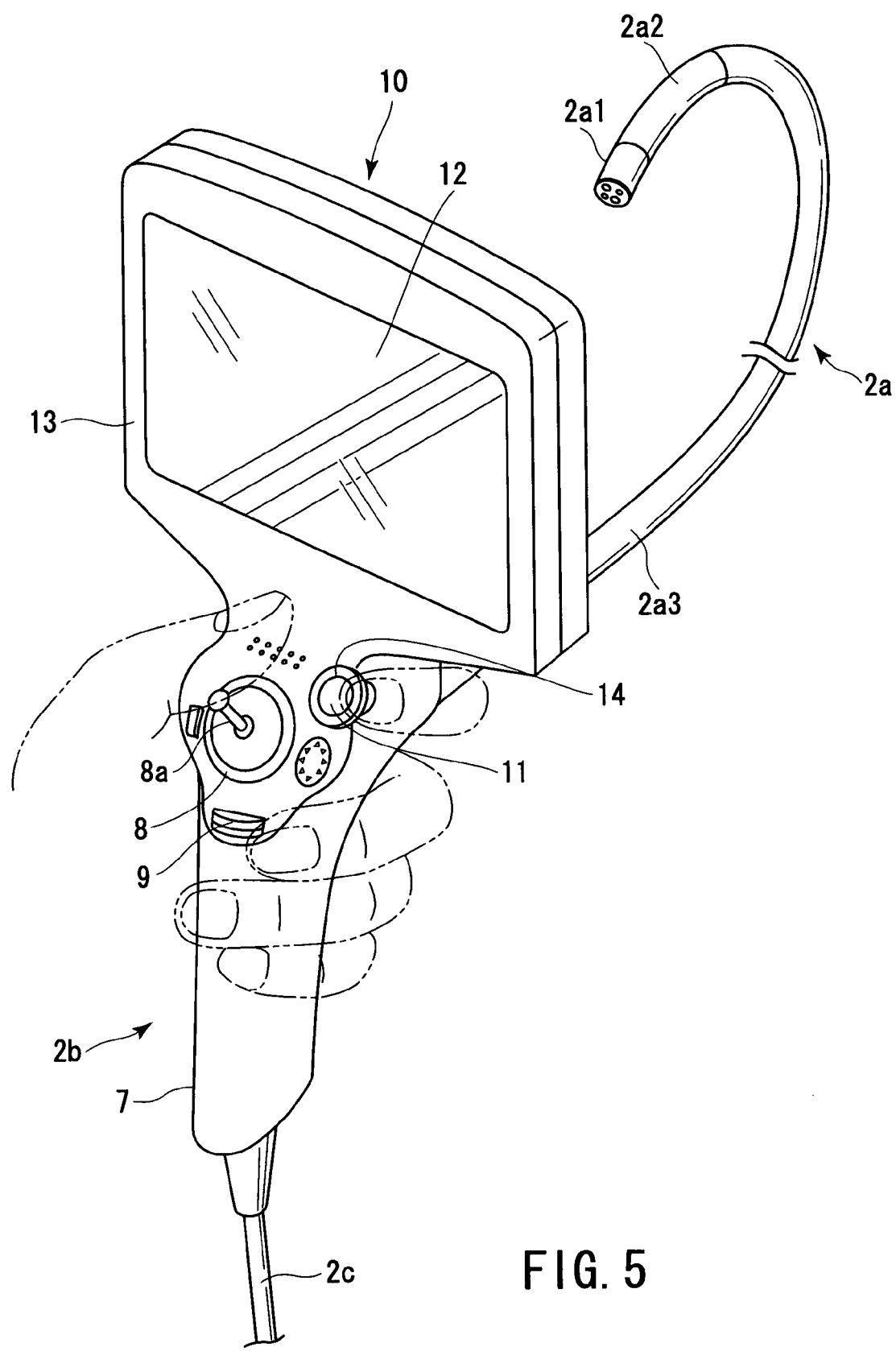
FIG. 5 is a perspective view illustrating a second state example in which the grip of the operation section incorporated in the endoscope apparatus of the first embodiment is gripped by one hand of an operator.
Figure 6:
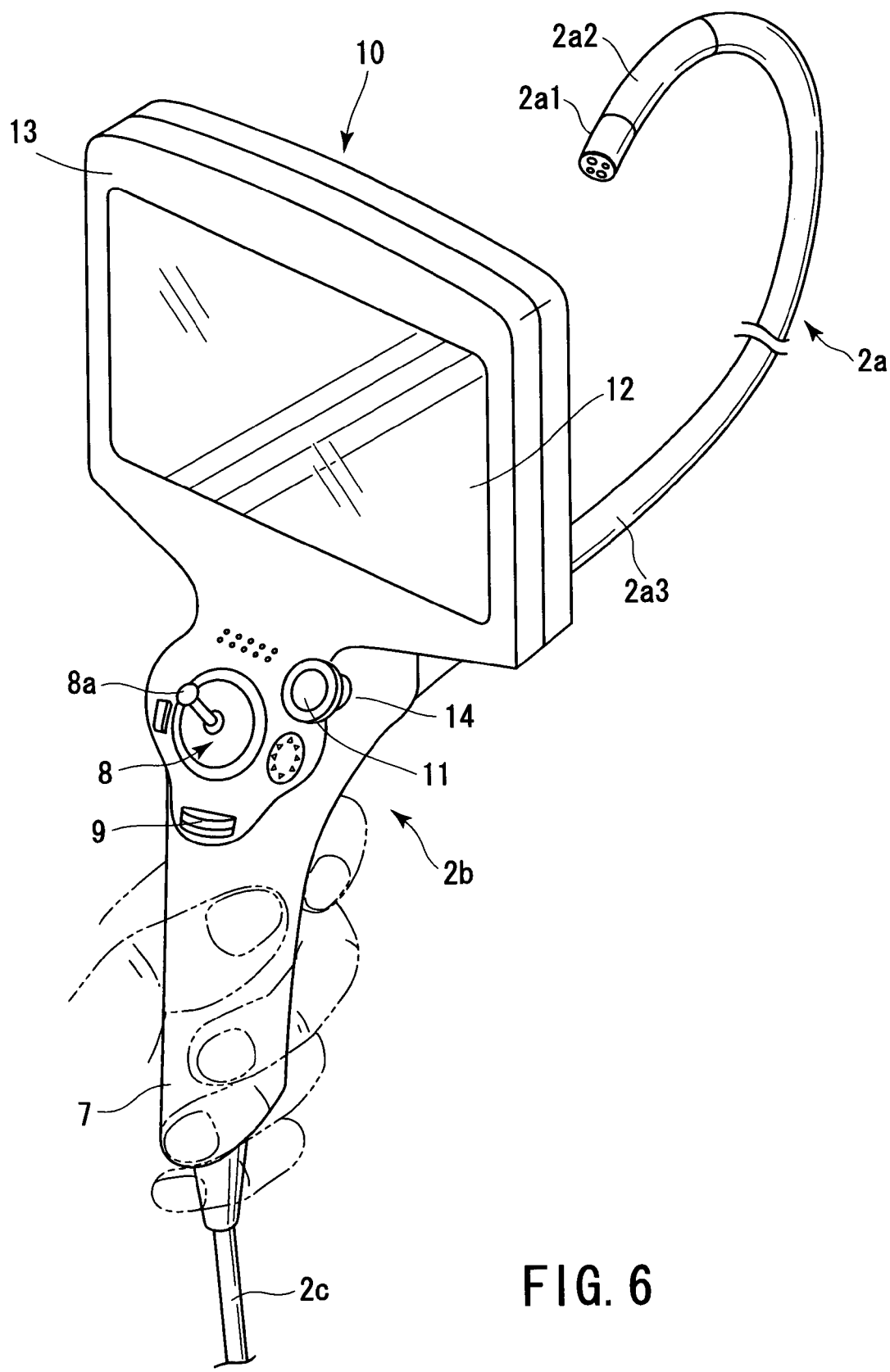
FIG. 6 is a perspective view illustrating a state in which the lower portion of the grip of the operation section incorporated in the endoscope apparatus of the first embodiment is gripped by one hand of an operator.
Figure 7:
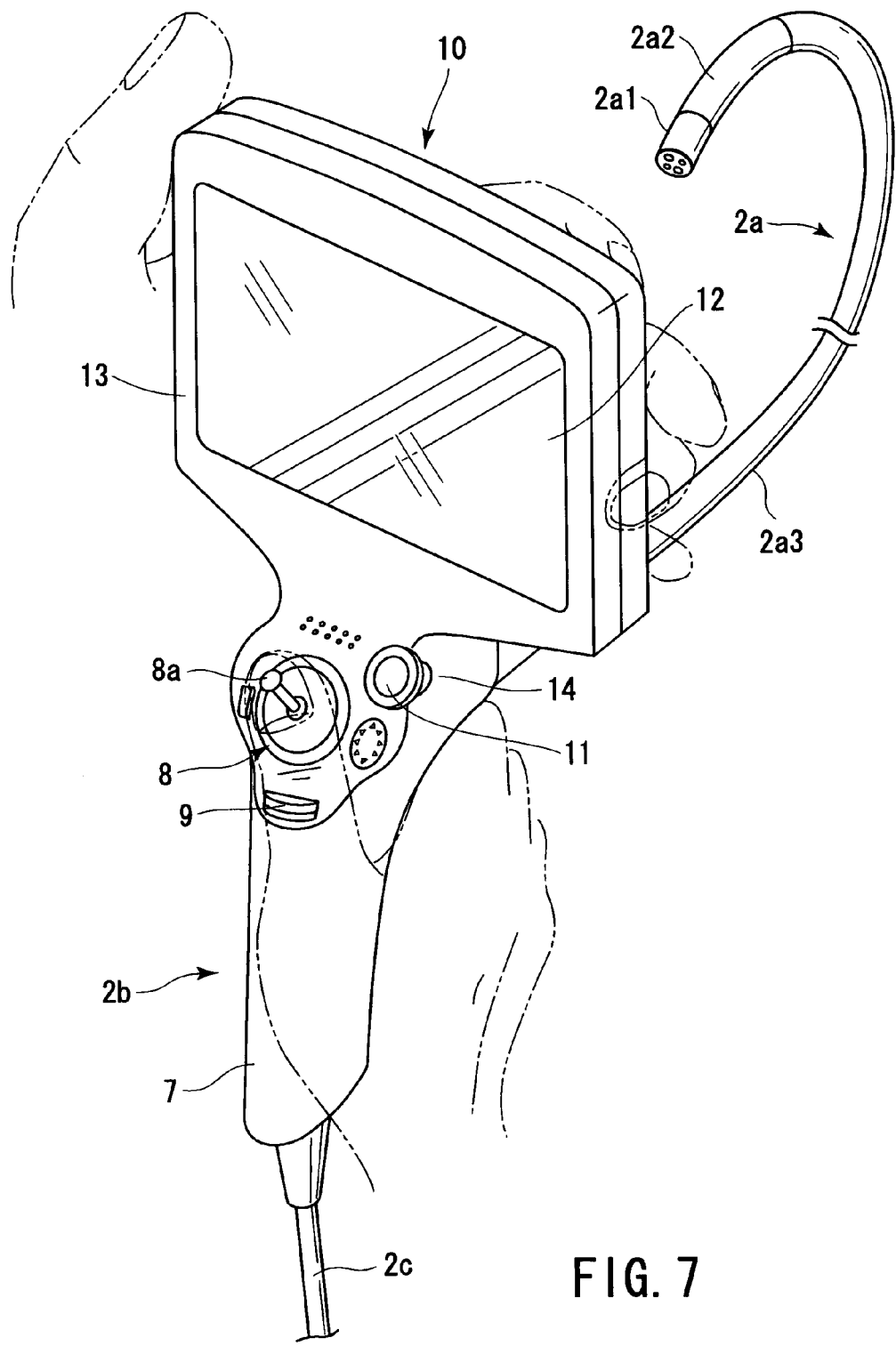
FIG. 7 is a perspective view illustrating a state in which the grip of the operation section incorporated in the endoscope apparatus of the first embodiment is gripped by both hands of an operator.

The operation of the above-described structure will now be described. When the industrial endoscope apparatus 1 is used, an operator grips the grip portion 7 of the operation section 2b. The operator can grip the grip portion 7 in various manners. FIGS. 4 and 5 show states in which the operator grips the entire grip portion 7 by one hand. FIG. 7 shows a state in which the operator grips the upper and lower portions of the grip portion 7 by both hands. Further, FIG. 6 shows a state in which the lower portion of the grip portion 7 is gripped by one hand. The gripping manners are not limited to these, though. With the grip portion 7 gripped, the insertion section 2a of the scope section 2 is inserted into a to-be-inspected space to inspect the space using the endoscope.

Figure 8:
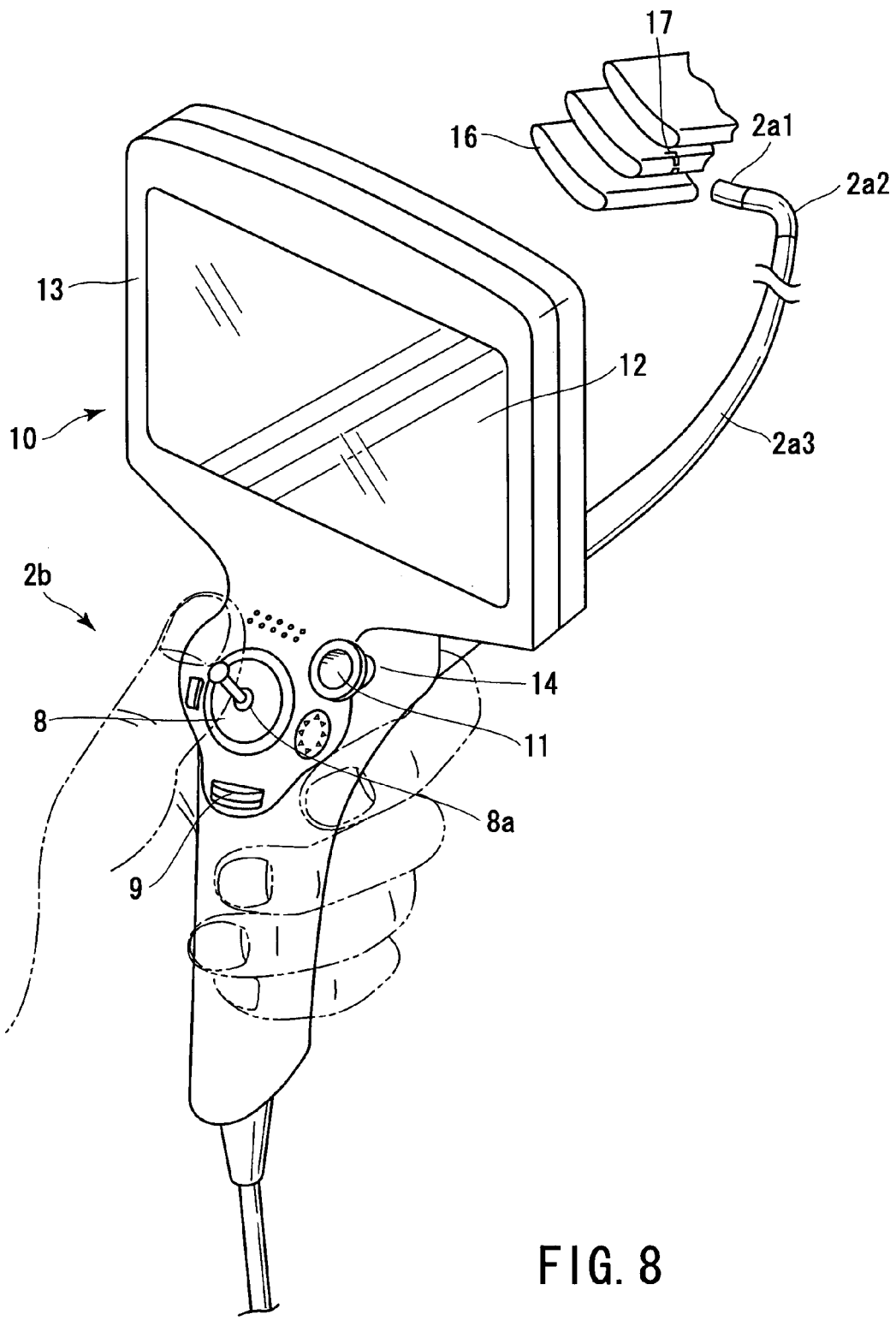
FIG. 8 is a perspective view illustrating a state assumed when an inspection is performed using the endoscope of the first embodiment.

When an inspection is performed using the endoscope, the CCD of the observation optical system in the head portion 2a1 picks up an endoscopic observation image as shown in FIG. 8. The CCD converts, into an electrical signal, image data corresponding to the endoscopic observation image. The electrical signal is transmitted to the camera control unit via the electric cord. The camera control unit converts the electrical signal into a video signal and outputs it to the display panel 12 of the monitor section 10 via the electric cord. As a result, the endoscopic observation image is displayed on the display panel 12 of the monitor section 10. More specifically, FIG. 8 shows a state in which the insertion section 2a of the scope section 2 is inserted into the inner space of an object, such as a turbine, thereby observing a crack 17 of a blade 16 contained in the space.

During an inspection using the endoscope, the bending operation unit 8 of the operation section 2b is operated while observing an endoscopic observation image on the display panel 12 of the monitor section 10. At this time, an operator grips the grip portion 7 of the operation section 2b by one hand, and operates the joystick 8a of the bending operation unit 8, using, for example, the thumb of the one hand, as shown in FIG. 8. Accordingly, the joystick 8a is inclined in an arbitrary direction. As a result of this remote control, the bendable portion 2a2 of the scope section 2 is bent in a direction corresponding to the operation direction of the joystick 8a.

Figure 9:
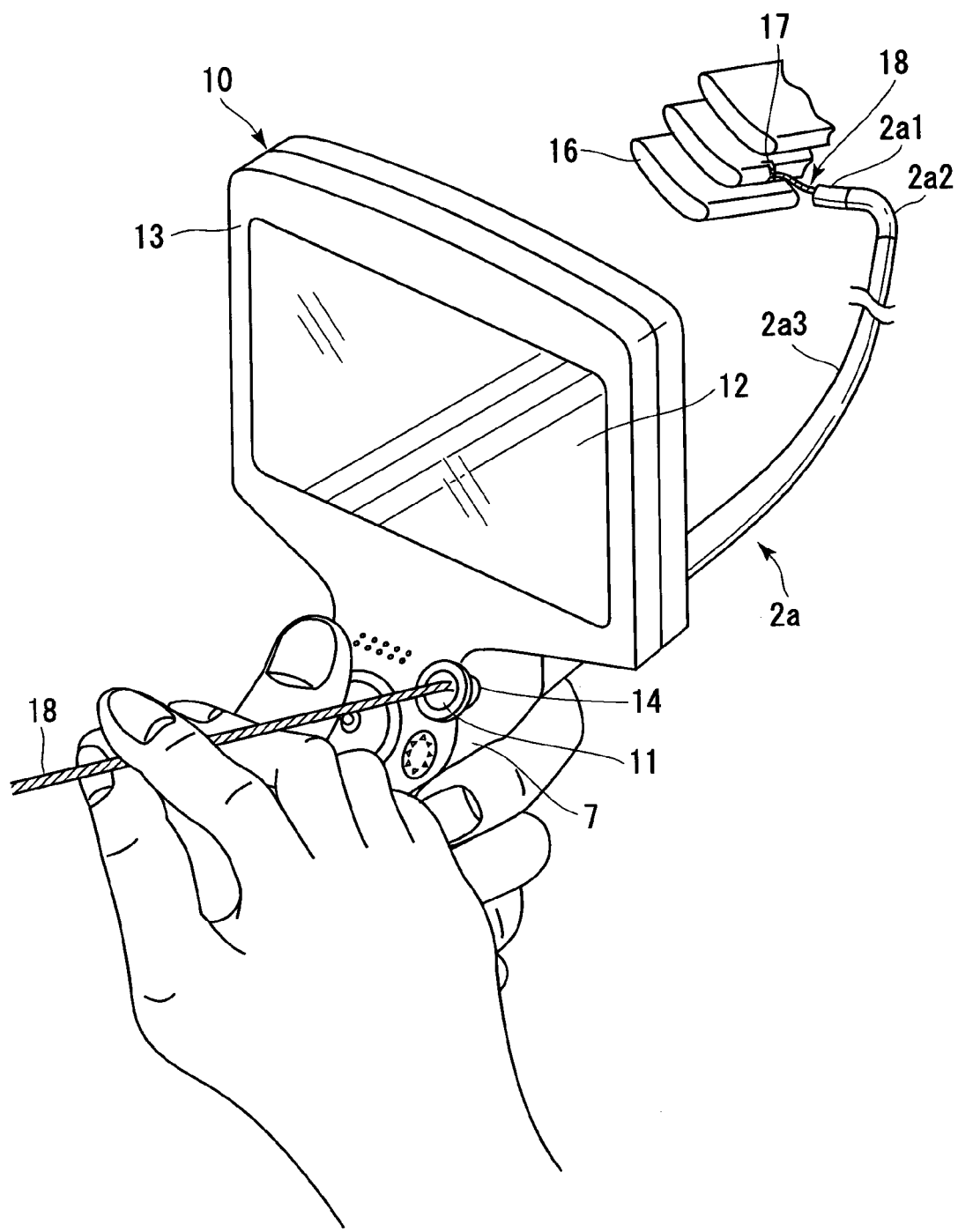
FIG. 9 is a perspective view illustrating a state in which a treatment instrument, such as forceps, is used during an inspection utilizing the endoscope of the first embodiment.

When the treatment instrument 18, such as forceps, is used, the treatment instrument 18 is inserted through the forceps port 11 defined by the forceps-port constructing member 14 as shown in FIG. 9. The forceps port 11 is located near the display panel 12 of the monitor section 10 and near the bending operation unit 8 as shown in FIG. 7. The operator performs the insertion operation while simultaneously observing the endoscopic observation image on the display panel 12, the operation of the being operation unit 8 by the left hand, and the operation of the wire 18a of the treatment instrument 18 by the right hand. Utilizing the inserted treatment instrument 18, a foreign material, for example, is removed from the space.

The above-described structure has the following advantage. In the industrial endoscope apparatus 1 according to the embodiment, the forceps port 11 defined by the forceps-port constructing member 14 is provided at the grip portion 7 of the operation section 2b near the display panel 12 of the monitor section 10 and near the bending operation unit 8. Accordingly, the operator can perform the insertion operation of the treatment instrument while simultaneously observing the endoscopic observation image on the display panel 12, the operation of the bending operation unit 8 by the left hand, and the operation of the treatment instrument 18 by the right hand. As a result, in addition to the bending operation utilizing the operation of the bending operation unit 8 by the left hand, the operation of the treatment instrument 18 by the right hand can also be performed on the grip portion 7 of the operation section 2b. In other words, these operations can be easily performed.

Figure 10:
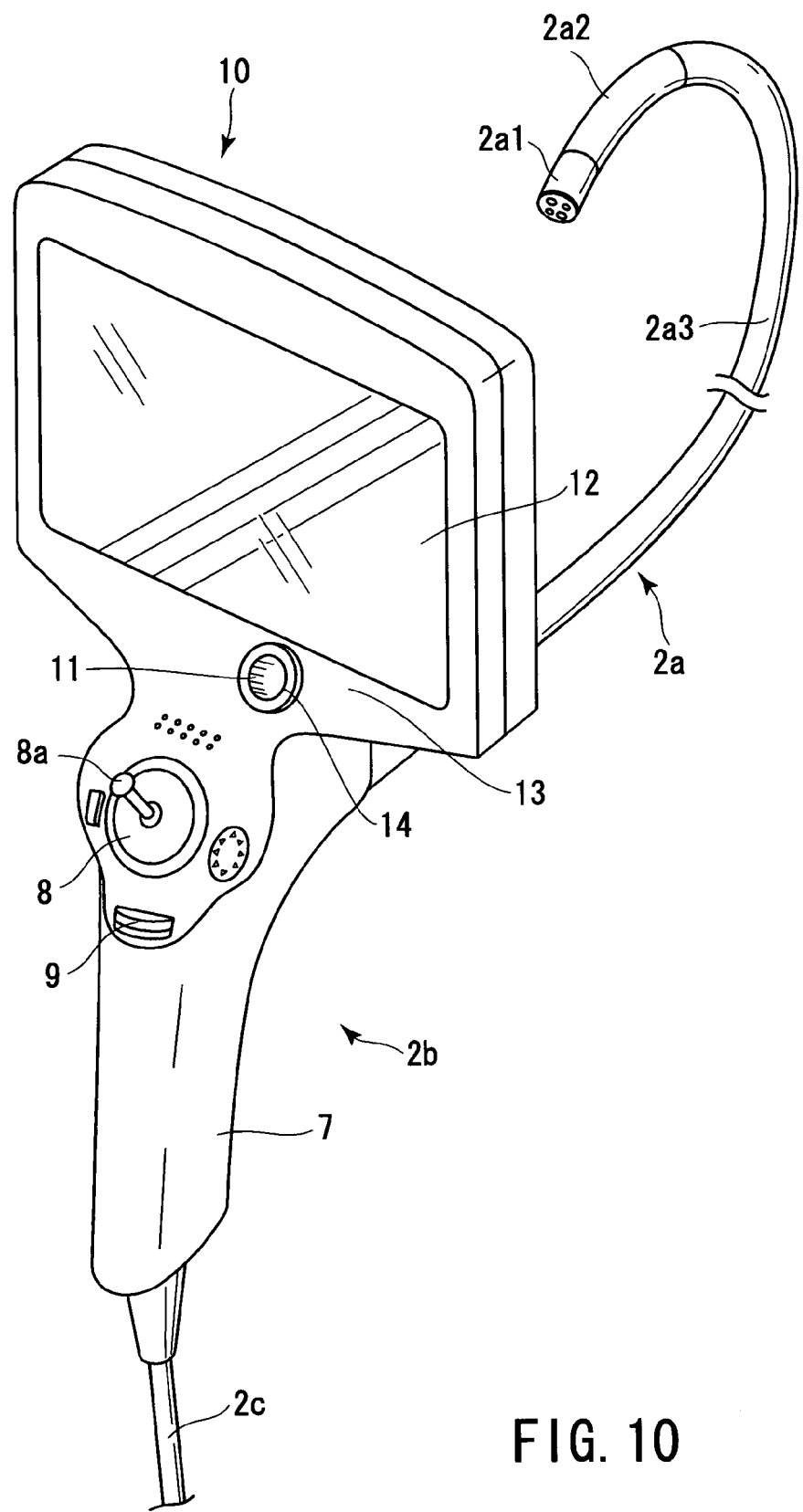
FIG. 10 is a perspective view illustrating the outward appearance of an operation section incorporated in an industrial endoscope apparatus according to a second embodiment.
Figure 11:
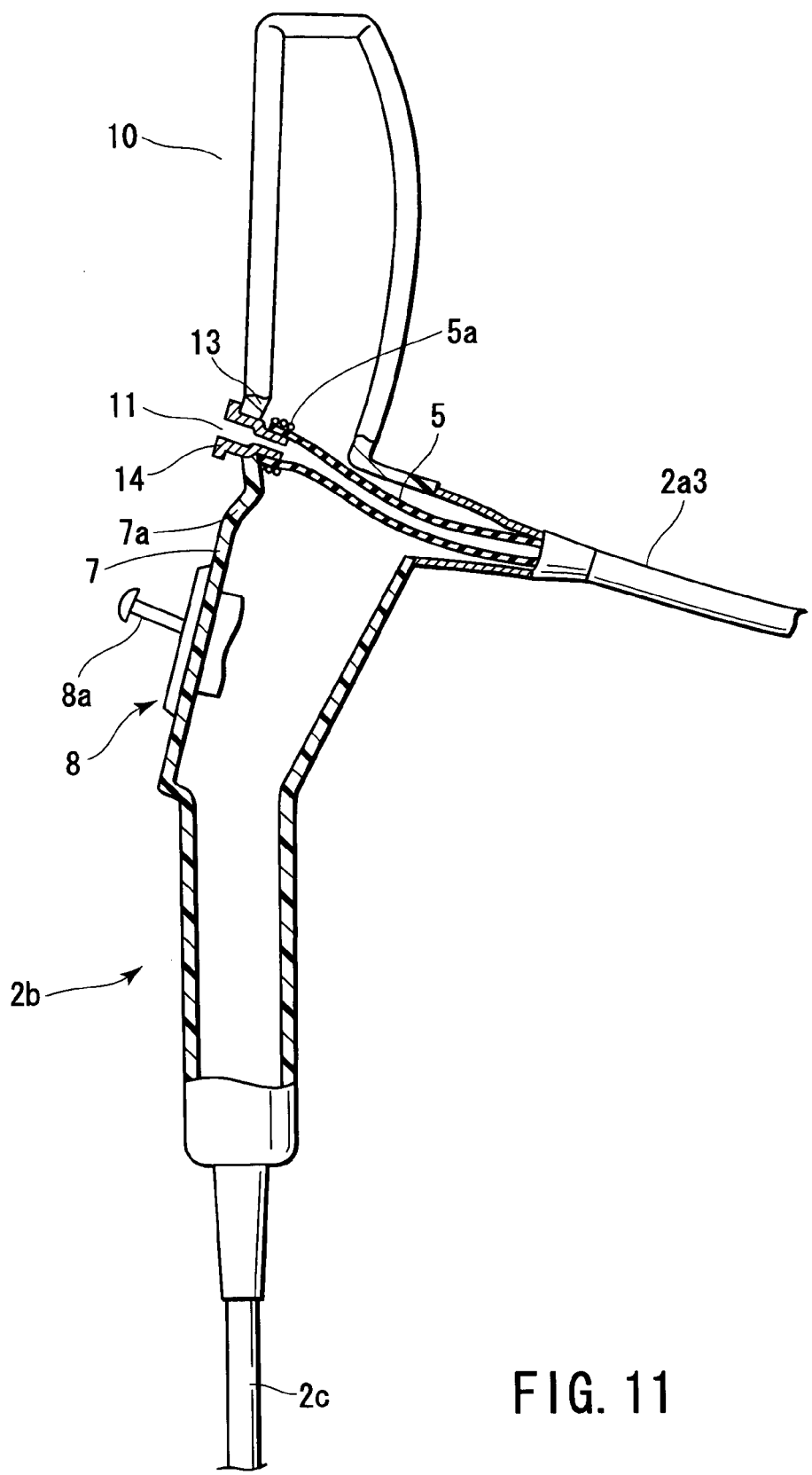
FIG. 11 is a side view partly in section illustrating the operation section of the endoscope apparatus of the second embodiment.

FIGS. 10 and 11 illustrate a second embodiment of the invention. The second embodiment is obtained by changing, in the manner described below, the structure of the operation section 2b incorporated in the industrial endoscope apparatus 1 of the first embodiment (shown in FIGS. 1A to 9). The basic structure of the second embodiment is substantially the same as that of the first embodiment. Therefore, in the second embodiment, elements similar to those of the first embodiment are denoted by corresponding reference numerals and are not described.

In the operation section 2b of the second embodiment, the forceps port 11 is provided in the frame 13 of the monitor section 10. As shown in FIG. 10, the forceps-port constructing member 14 providing the forceps port 11 is located at a lower side portion of the lower edge of the frame 13. This means that the forceps port 11 is located closer to an operator, therefore the operator can easily operate the treatment instrument 18, such as a forceps. Further, as shown in FIG. 11, the proximal open end 5a of the inner channel 5 is secured to the inner end of the forceps-port constructing member 14.

Figure 12:
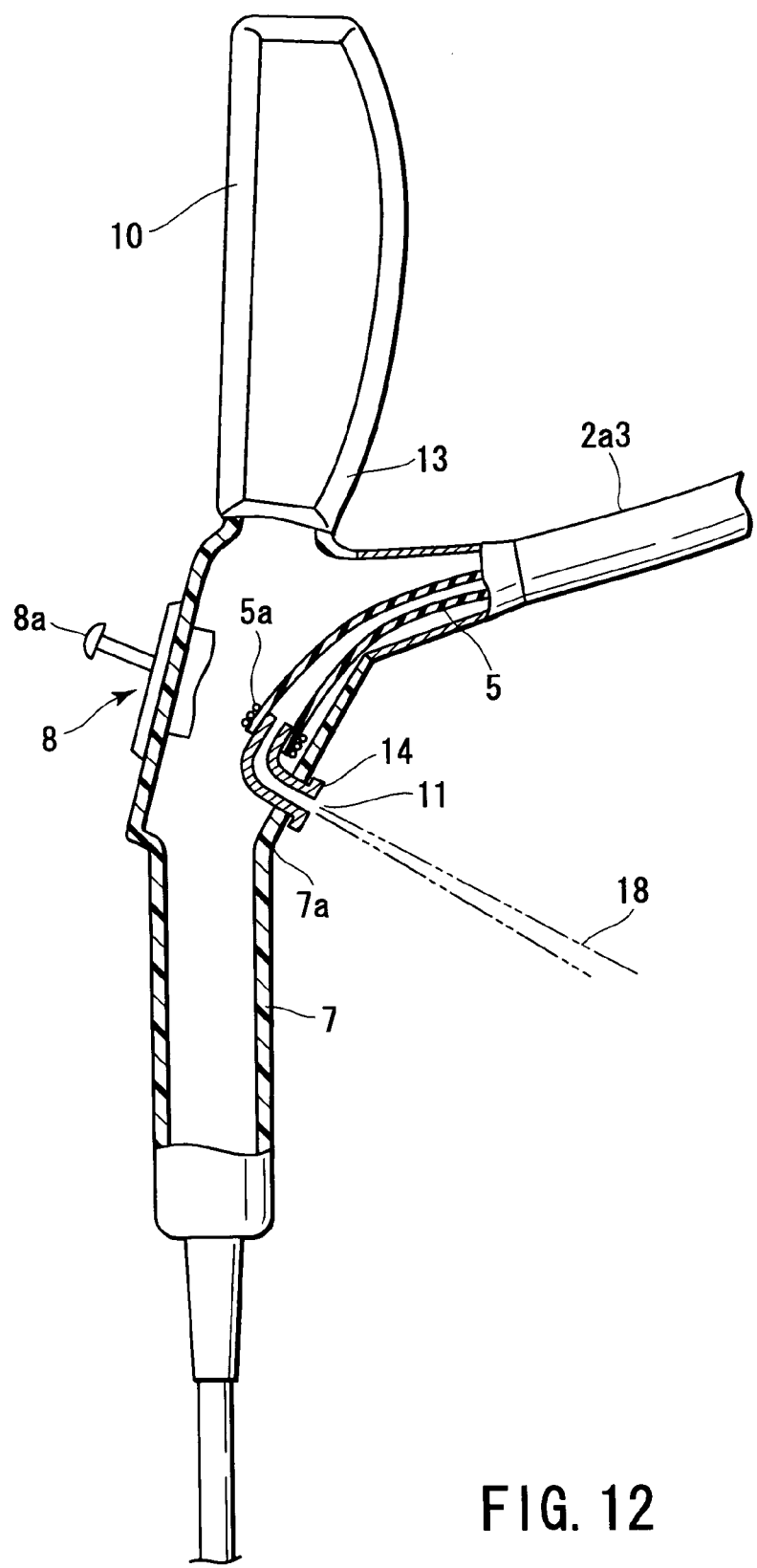
FIG. 12 is a side view partly in section illustrating the operation section of an industrial endoscope apparatus according to a third embodiment.

FIG. 12 shows a third embodiment of the invention. The third embodiment is obtained by changing, in the manner described below, the structure of the operation section 2b incorporated in the industrial endoscope apparatus 1 of the first embodiment (shown in FIGS. 1A to 9).

In the operation section 2b of the third embodiment, a downwardly opening forceps port 11 is formed in the rear surface of the casing 7a of the grip portion 7 at a position lower than the position opposing the bending operation unit 8. Accordingly, even if the proximal portion of the treatment instrument 18, such as a forceps, inserted through the forceps port 11, i.e., the portion of the instrument extending outside the forceps port 11, hangs from the port, it does not interfere with the operation of the bending operation unit 8, since it hangs along the rear surface of the grip portion 7.

Figure 13:
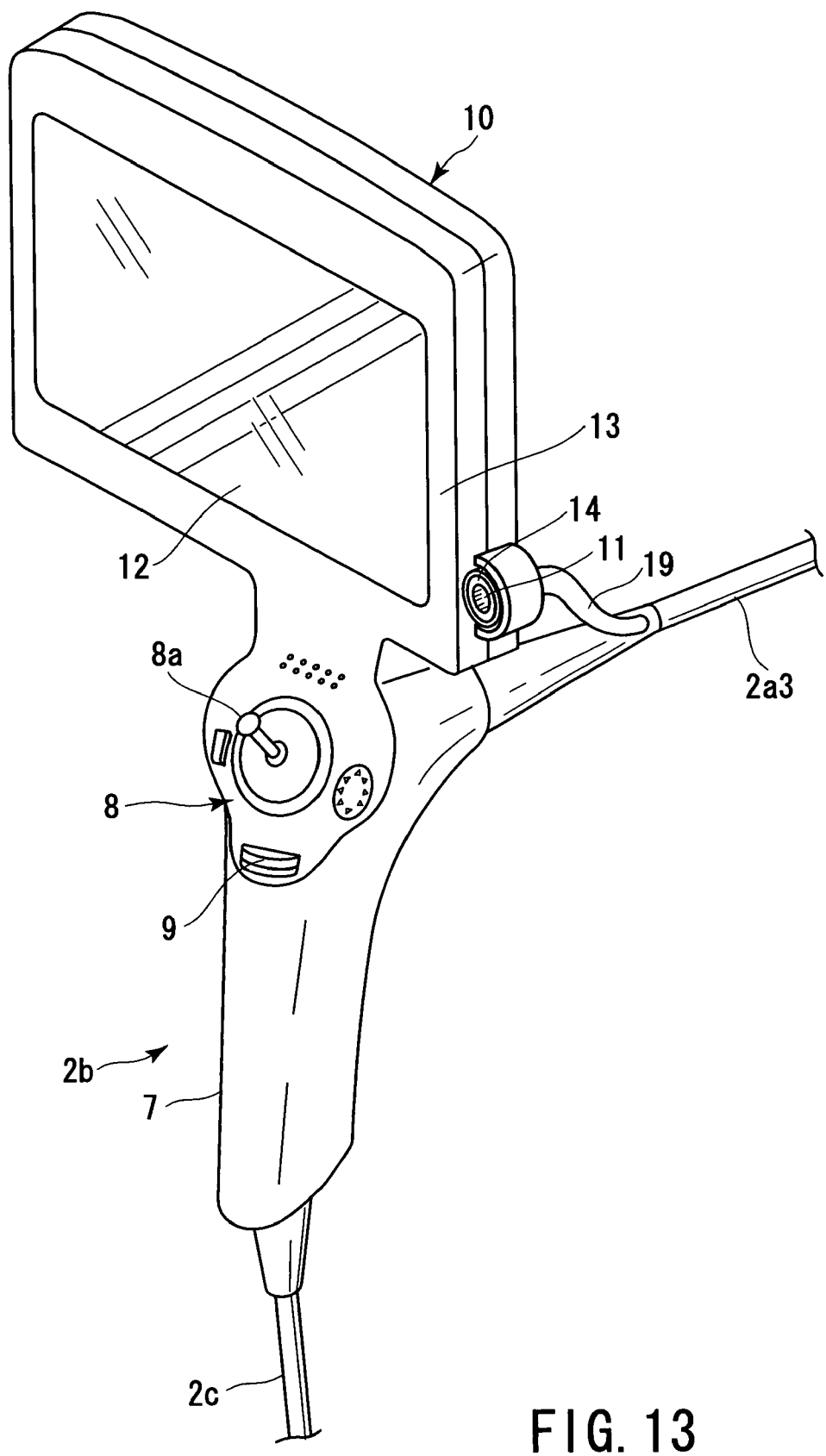
FIG. 13 is a perspective view illustrating the outward appearance of an operation section incorporated in an industrial endoscope apparatus according to a fourth embodiment.
Figure 14:
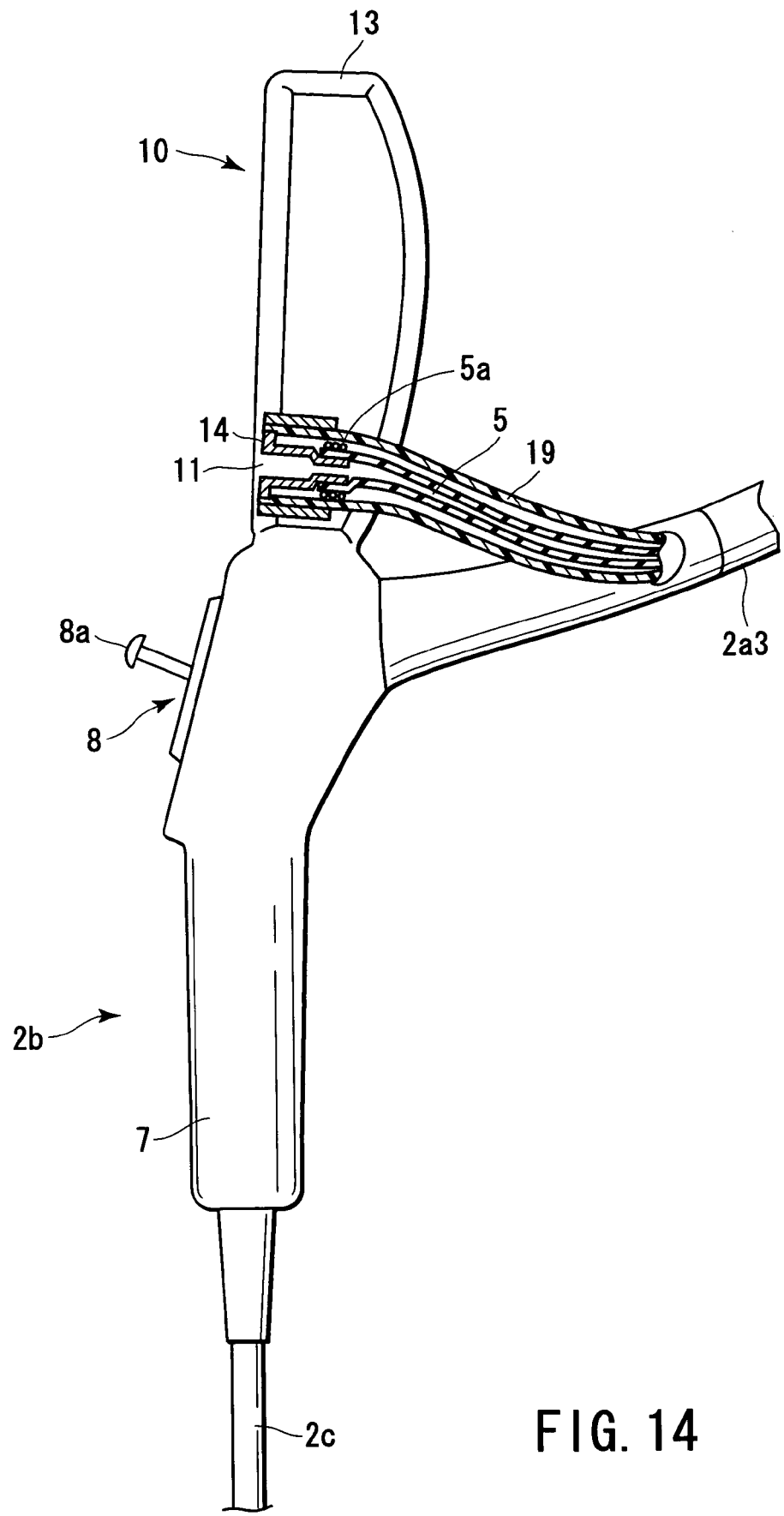
FIG. 14 is a side view partly in section illustrating the operation section of the endoscope apparatus of the fourth embodiment.

FIGS. 13 and 14 illustrate a fourth embodiment of the invention. The fourth embodiment is obtained by changing, in the manner described below, the structure of the operation section 2b incorporated in the industrial endoscope apparatus 1 of the first embodiment (shown in FIGS. 1A to 9).

In the operation section 2b of the fourth embodiment, the forceps port 11 is provided at the right side of the frame 13 of the monitor section 10. As shown in FIG. 14, a tubular tube-support member 19 is interposed between a side portion of the frame 13 and the flexible tube portion 2a3. The forceps-port constructing member 14 providing the forceps port 11 is secured to one end of the tube-support member 19. The proximal end of the inner channel 5 is extended from the other end of the tube-support member 19 into the tube-support member 19, with the result that the proximal open end 5a of the inner channel 5 is coupled to the inner end of the forceps-port constructing member 14.

As described above, in the operation section 2b of this embodiment, the forceps port 11 is located at a side of the frame 13 of the monitor section 10, i.e., located away from the operation range of the joystick 8a of the bending operation unit 8. Therefore, the forceps port 11 does not interfere with the operation of the joystick 8a. It is not always needed to locate the forceps port 11 at the right side of the frame 13, but the forceps port 11 may be located at the upper portion or left side of the frame 13.

Figure 15:
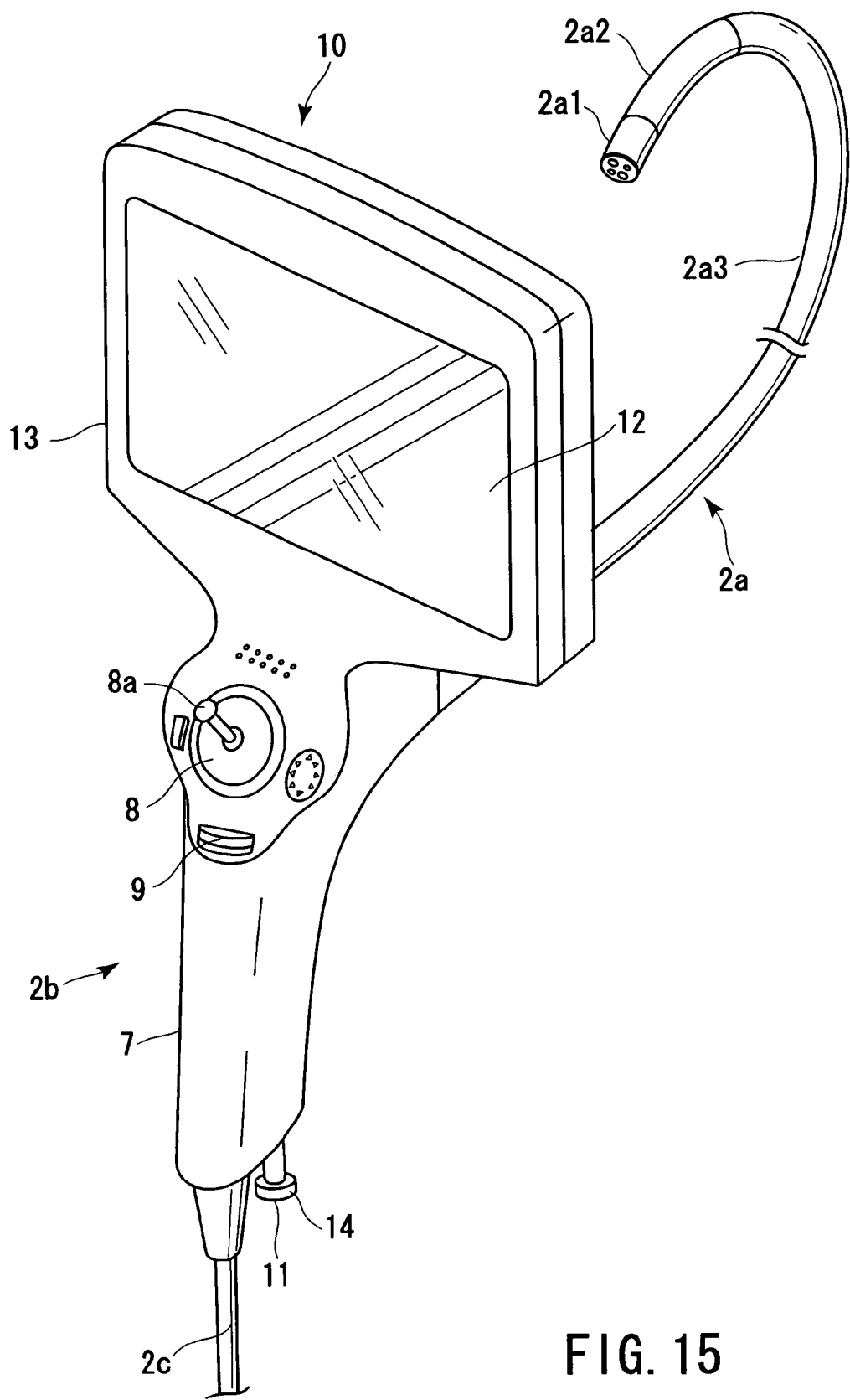
FIG. 15 is a perspective view illustrating the outward appearance of an operation section incorporated in an industrial endoscope apparatus according to a fifth embodiment.
Figure 16:
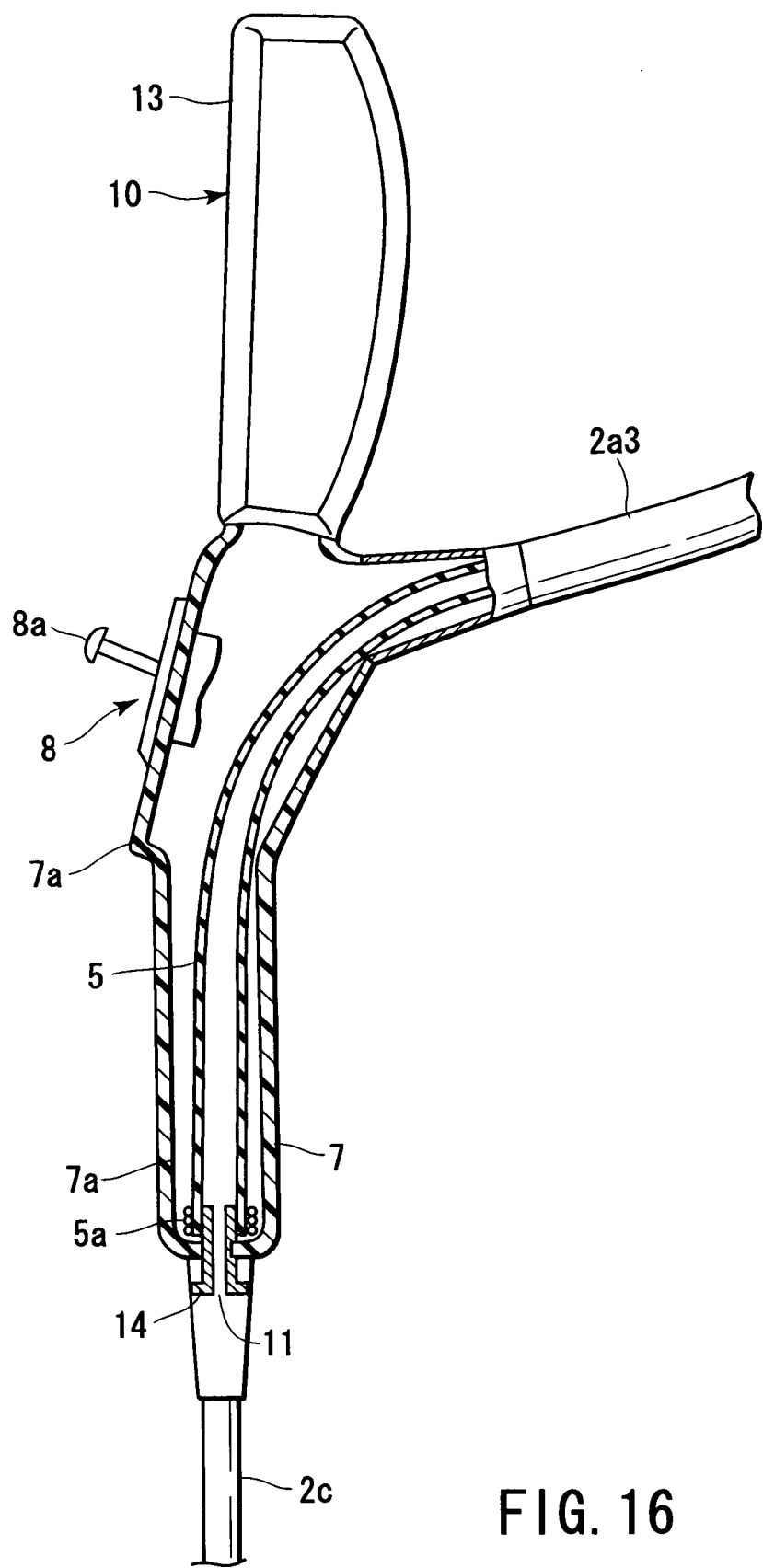
FIG. 16 is a side view partly in section illustrating the operation section of the endoscope apparatus of the fifth embodiment.

FIGS. 15 and 16 illustrate a fifth embodiment of the invention. The fifth embodiment is obtained by changing, in the manner described below, the structure of the operation section 2b incorporated in the industrial endoscope apparatus 1 of the first embodiment (shown in FIGS. 1A to 9).

In the operation section 2b of the fifth embodiment, a downwardly opening forceps port 11 is provided at the lower end of the casing 7a of the grip portion 7.

In this structure, even if the proximal portion of the treatment instrument 18, such as a forceps, inserted through the forceps port 11 hangs down from the forceps port 11, it does not interfere with the operation of the bending operation unit 8 since it is positioned at the lower end of the casing 7a away from the unit 8.

Figure 17:
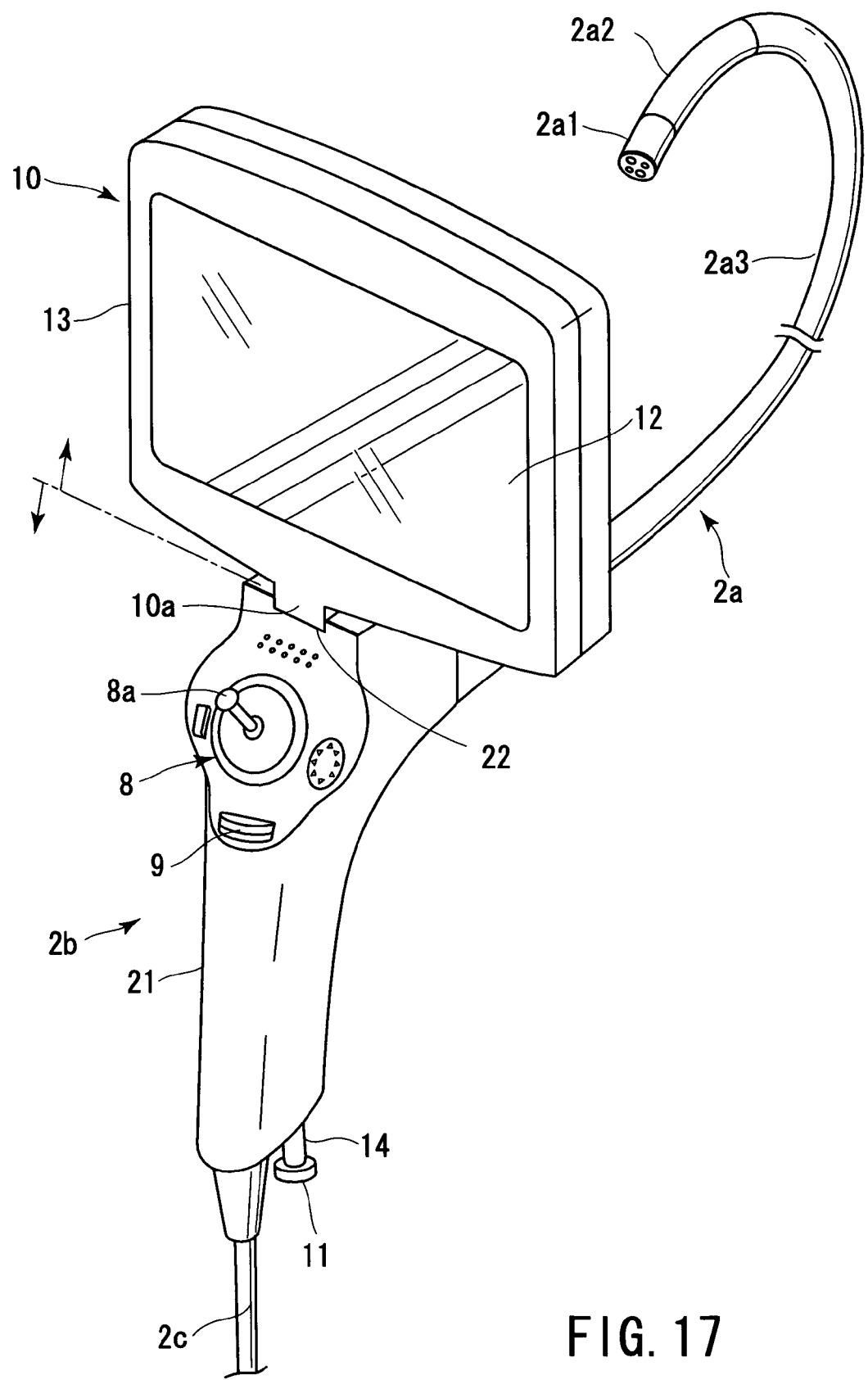
FIG. 17 is a perspective view illustrating the outward appearance of an operation section incorporated in an industrial endoscope apparatus according to a sixth embodiment.

FIG. 17 shows a sixth embodiment of the invention. The sixth embodiment is obtained by changing, in the manner described below, the structure of the operation section 2b of the industrial endoscope apparatus 1 according to the fifth embodiment (shown in FIGS. 15 and 16).

In the operation section 2b of the sixth embodiment, the monitor section 10 is detachably attached to a grip portion 21. A monitor attachment recess 22 is defined in the upper end of the grip portion 21. A coupling portion 10a projecting from the lower end of the monitor section 10 is detachably fitted in the monitor attachment recess 22.

In this embodiment, the monitor section 10 can be disengaged from the grip portion 21 when necessary. When the monitor section 10 is detached, the weight of the grip portion 21 is reduced, thereby facilitating the operation of the grip portion 21.

Figure 18:
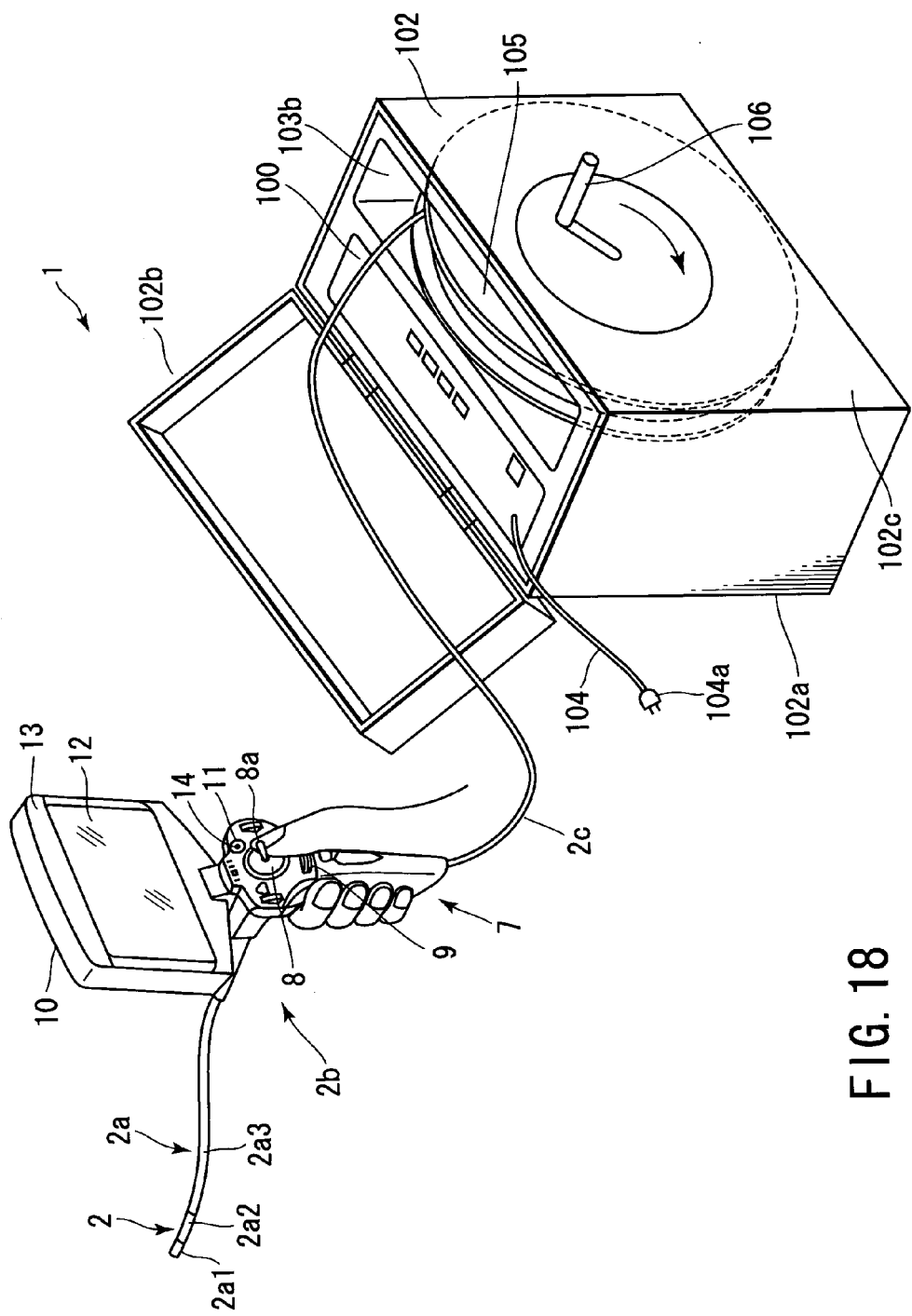
FIG. 18 is a perspective view illustrating the outward appearance of an industrial endoscope apparatus according to a seventh embodiment of the invention.

FIG. 18 shows a seventh embodiment of the invention. The seventh embodiment is obtained by changing, in the manner described below, the structure of the endoscope case 102 of the industrial endoscope apparatus 1 according to the first embodiment (shown in FIGS. 1A to 9).

In the endoscope case 102 of this embodiment, a winding drum 105 is contained in the second chamber 103b. A handle 106 incorporated in the winding drum 105 is located on the front panel 102c of the endoscope case 102.

In this embodiment, when the handle 106 is rotated in the direction indicated by the arrow in FIG. 18, the insertion section 2a of the scope section 2, the operation section 2b and the universal cord 2c are wound on the winding drum 105. Thus, the scope section 2 can be easily housed after it is used.

Figure 19:
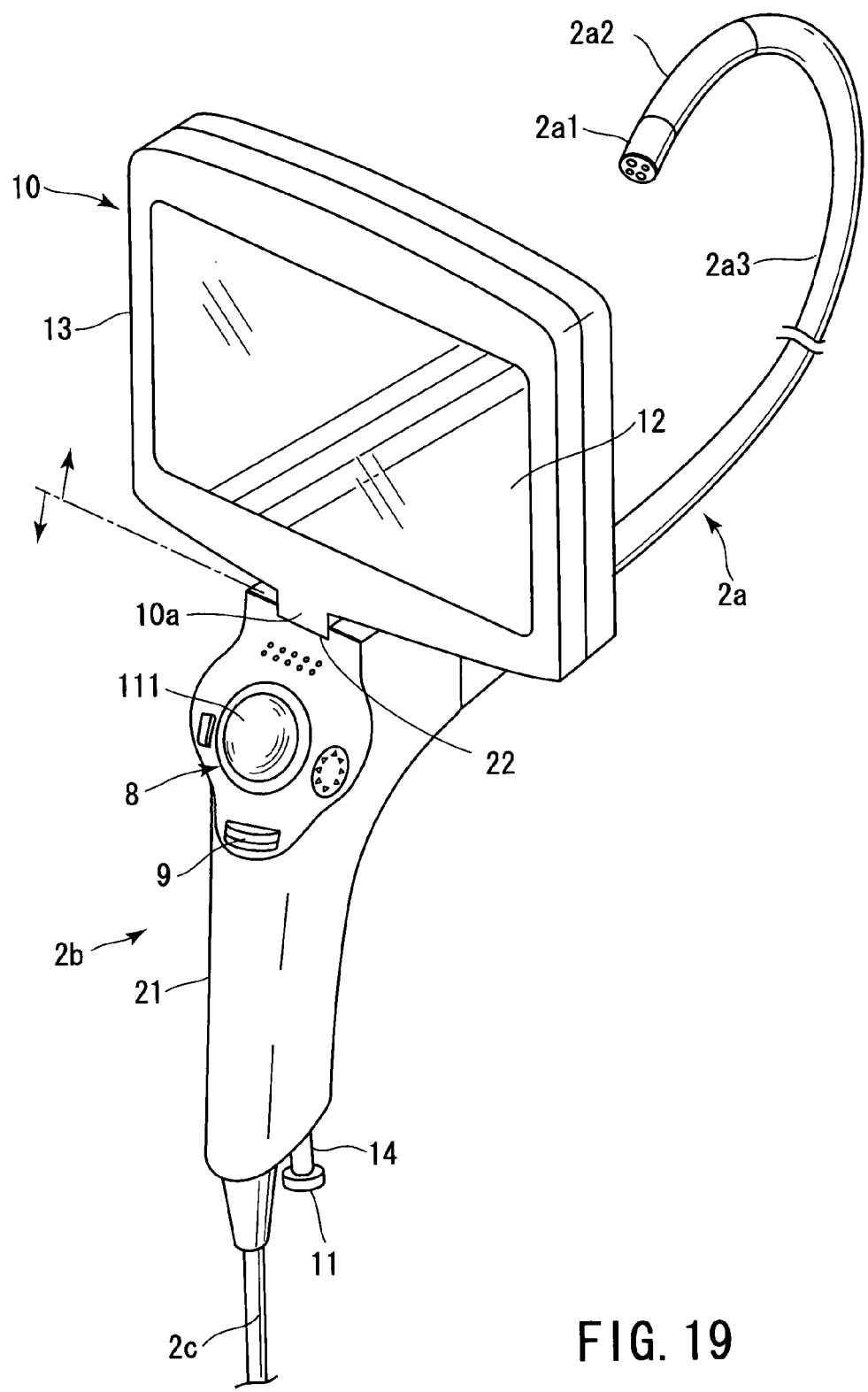
FIG. 19 is a perspective view illustrating the outward appearance of an operation section incorporated in an industrial endoscope apparatus according to an eighth embodiment.

FIG. 19 shows an eighth embodiment of the invention. The eighth embodiment is obtained by replacing, with a track ball 111, the joystick 8a of the bending operation unit 8 incorporated in the operation section 2b of the endoscope 1 according to the sixth embodiment (shown in FIG. 17).

Figure 20:
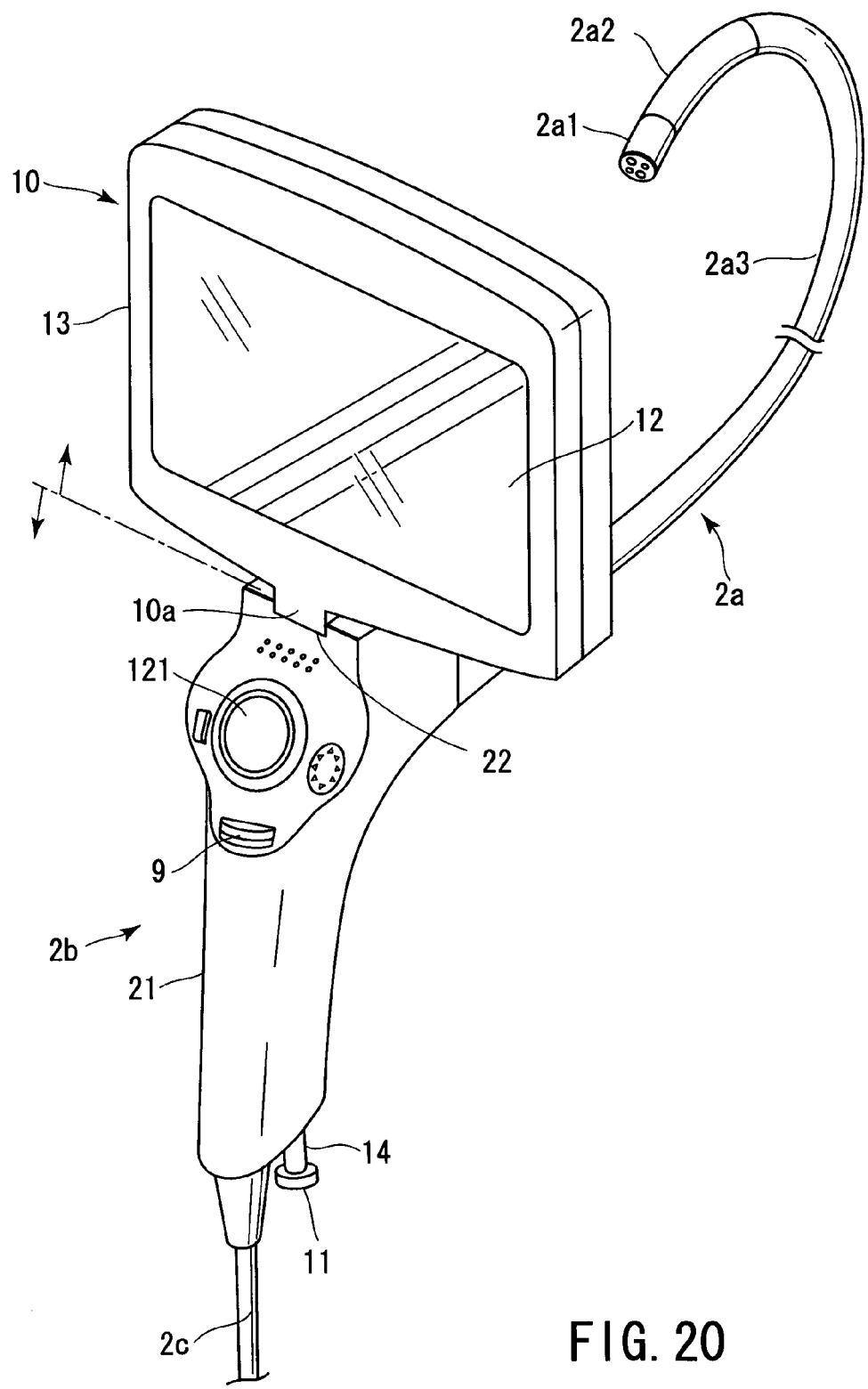
FIG. 20 is a perspective view illustrating the outward appearance of an operation section incorporated in an industrial endoscope apparatus according to a ninth embodiment.

FIG. 20 shows a ninth embodiment of the invention. The ninth embodiment is obtained by replacing, with a track pad 121, the joystick 8a of the bending operation unit 8 incorporated in the operation section 2b of the endoscope 1 according to the sixth embodiment (shown in FIG. 17).

Figure 21:
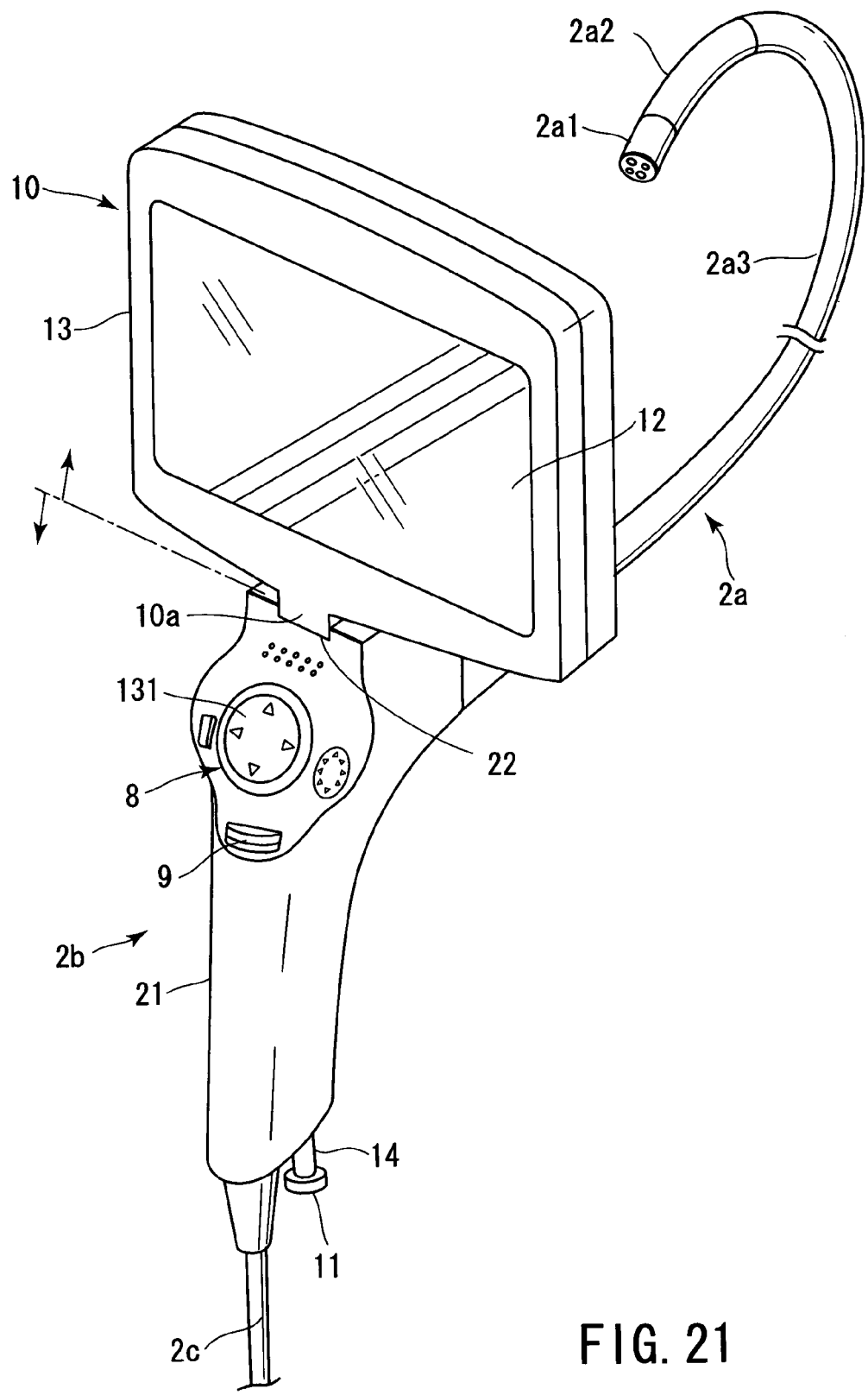
FIG. 21 is a perspective view illustrating the outward appearance of an operation section incorporated in an industrial endoscope apparatus according to a tenth embodiment.

FIG. 21 shows a tenth embodiment of the invention. The tenth embodiment is obtained by replacing, with a pointing device such as a four- or eight-directional instruction key 131, the joystick 8a of the bending operation unit 8 incorporated in the operation section 2b of the endoscope 1 according to the sixth embodiment (shown in FIG. 17).

The present invention is not limited to the above-described embodiments, but may be modified in various ways without departing from the scope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
a flexible slender insertion section inserted from its distal end into a to-be-inspected space, the insertion section being constructed from a distal portion for picking up an observation image, a bendable portion to be bent, and a slender flexible tube portion, which are coupled, and having a proximal portion on an opposite side of a distal portion of the flexible tube portion;
a pistol grip portion to be gripped by an operator, the pistol grip having a longitudinal axis extending from a first end to a second end that is opposite the first end,
an operation section coupled to a proximal end of the insertion section, the operation section, coupled to the first end of the pistol grip portion, having a bending operation portion which bends the bendable portion, and a display portion formed of a display panel which displays the observation image provided on a frame integrally attached to the first end of the pistol grip portion, and
wherein the insertion section has a channel provided so that a treatment instrument extends out from a distal open end provided on the distal portion, and wherein a proximal open end for inserting the treatment instrument into the channel is provided at the second end of the pistol grip portion.

2. The endoscope apparatus according to claim 1, wherein the pistol grip portion has a grip which can be gripped by one hand of the operator.

3. The endoscope apparatus according to claim 2, wherein said pistol grip portion has a casing and a forceps-port constructing member, and
the forceps-port constructing member is coupled to the second end of said grip end so as to provide a forceps-port.

4. The endoscope apparatus according to claim 2, wherein said frame has a connection portion detachable from said pistol grip portion.

5. The endoscope apparatus according to claim 1, wherein the display portion is detachable from the pistol grip portion.

6. The endoscope apparatus according to claim 1, wherein the bending operation portion is structured by a joystick.

7. The endoscope apparatus according to claim 1, wherein the bending operation portion is structured by a trackball.

8. The endoscope apparatus according to claim 1, wherein the bending operation portion is a trackpad.

9. The endoscope apparatus according to claim 1, wherein the bending operation portion is structured by a four-directional instruction key.

10. The endoscope apparatus according to claim 1, wherein the bending operation portion is structured by an eight directional instruction key.

11. An endoscope apparatus comprising:
a slender insertion section inserted from its distal end into a to-be-inspected space, a distal end side of the insertion section including an observation optical system having a CCD for picking up a to-be-inspected object, a bendable portion to be bent, and a slender flexible tube portion, and a proximal portion on a rear end side of the insertion section being coupled to an operation section;
a pistol grip portion to be gripped by an operator, the pistol grip portion having a longitudinal axis extending from a first end to a second end,
an operation section coupled to a proximal end of the insertion section, the operation section having a bendable operation section which bends the bendable portion, the bendable operation section coupled to the first end of the pistol grip, and a display portion which displays the picked up to-be-inspected image provided on the bendable operation section,
wherein the insertion section has a channel which extends from the distal end portion to the second end of the pistol grip portion via the proximal portion, and wherein a treatment instrument is inserted into the channel from the insertion opening at the second end of the pistol grip portion and extends out from an open end on the distal end side.

* * * * *